US011135404B2

(12) United States Patent
Lagana' et al.

(10) Patent No.: US 11,135,404 B2
(45) Date of Patent: Oct. 5, 2021

(54) SAFETY CATHETER NEEDLE

(71) Applicant: SOL-MILLENNIUM SWISS R&D CENTER SA, Lugano (CH)

(72) Inventors: Matteo Lagana', Longone al Segrino (IT); Dario De Zolt, Fagnano Olona (IT)

(73) Assignee: SOL-MILLENNIUM SWISS R&D CENTER SA, Lugano (CH)

( * ) Notice: Subject to any disclaimer, the term of this patent is extended or adjusted under 35 U.S.C. 154(b) by 0 days.

(21) Appl. No.: 16/771,037

(22) PCT Filed: Dec. 12, 2018

(86) PCT No.: PCT/IB2018/059932
§ 371 (c)(1),
(2) Date: Jun. 9, 2020

(87) PCT Pub. No.: WO2019/123120
PCT Pub. Date: Jun. 27, 2019

(65) Prior Publication Data
US 2021/0187249 A1 Jun. 24, 2021

(30) Foreign Application Priority Data
Dec. 18, 2017 (IT) .......................... 102017000145675

(51) Int. Cl.
*A61M 25/06* (2006.01)
(52) U.S. Cl.
CPC . *A61M 25/0618* (2013.01); *A61M 2205/0222* (2013.01)
(58) Field of Classification Search
CPC .......... A61M 25/0618; A61M 25/0625; A61M 2005/325; A61M 25/0631; A61M 2205/0222
See application file for complete search history.

(56) References Cited

U.S. PATENT DOCUMENTS 5,300,045 A * 4/1994 Plassche, Jr. ....... A61M 5/3273
604/158
2008/0065015 A1 3/2008 Fiser et al.

FOREIGN PATENT DOCUMENTS

| EP | 1920796 A1 | 5/2008 |
| WO | 0006226 A1 | 2/2000 |
| WO | 2012016660 A1 | 2/2012 |

OTHER PUBLICATIONS

International Search Report and Written Opinion for Corresponding International Application No. PCT/IB2018/059932 (9 Pages) (dated Mar. 21, 2019).

* cited by examiner

*Primary Examiner* — Lauren P Farrar
*Assistant Examiner* — Hamza A Darb
(74) *Attorney, Agent, or Firm* — Lucas & Mercanti, LLP

(57) ABSTRACT

A safety catheter needle having a cannula removably inserted in a catheter and associated with a cannula holder is provided. The cannula has a proximal extremity attached to the cannula holder and a distal extremity close to a deformed part, with provision for a protection device associated with the catheter holder movably containing the cannula and moving within the catheter holder when the cannula is drawn out from the catheter. The protection device has a principal body containing a moving body rotating about an axis (M) at right angles to a longitudinal axis (W) of the cannula and capable of interacting with a fixed part of the catheter holder—while the cannula is being drawn out, bringing about rotation of the rotating moving body within the principal body and immobilizing the distal extremity of the cannula within the former.

11 Claims, 21 Drawing Sheets

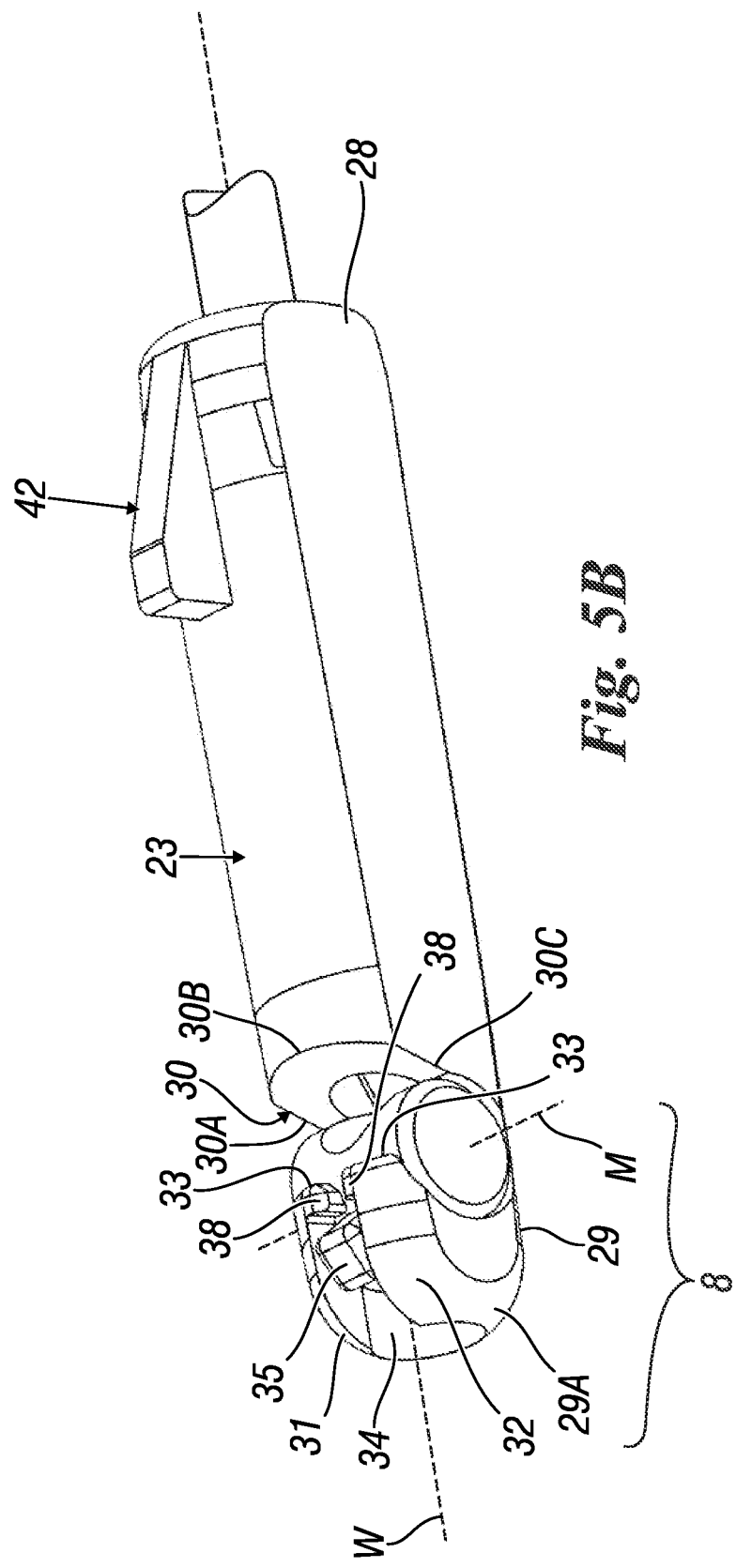

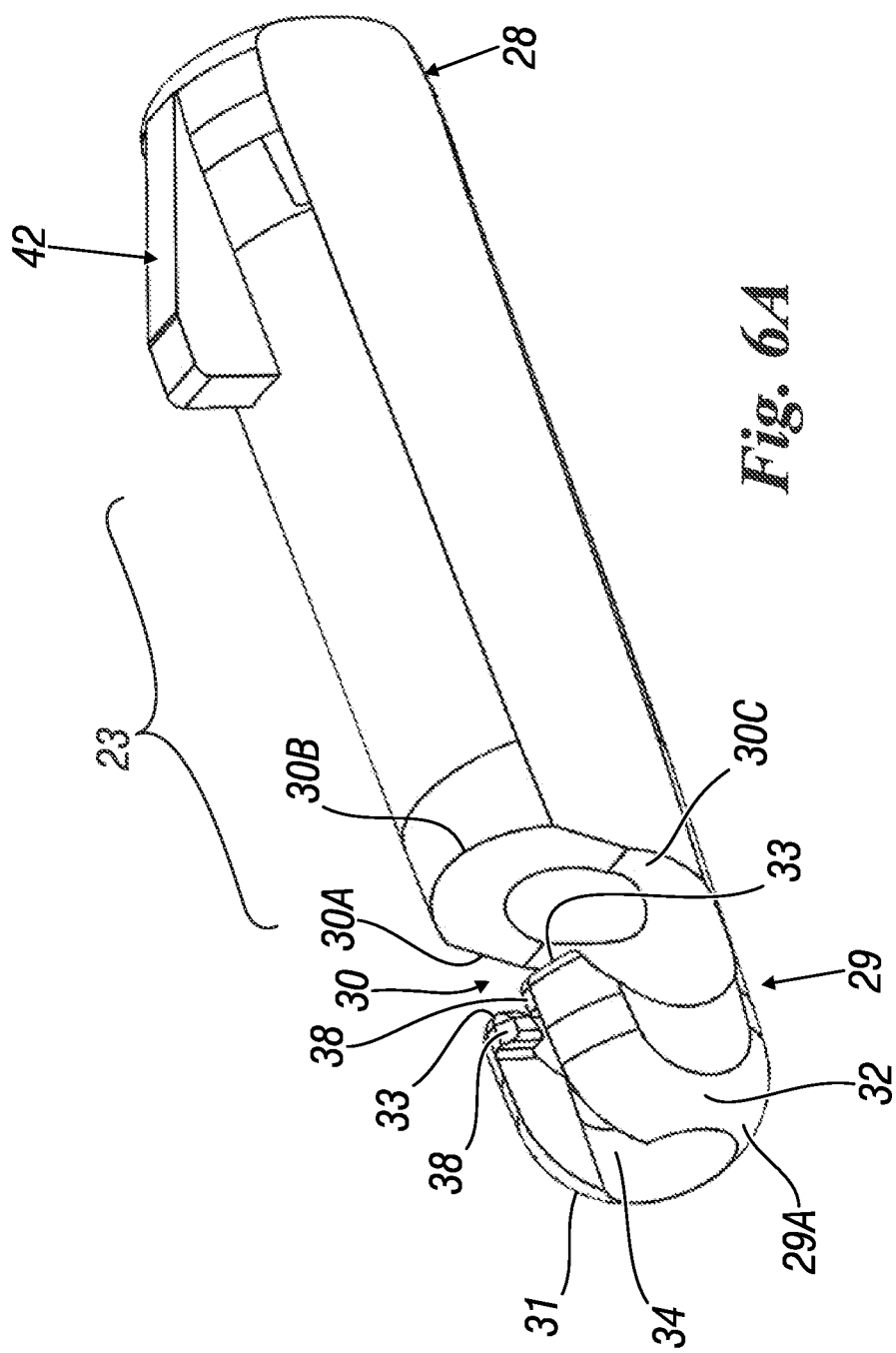

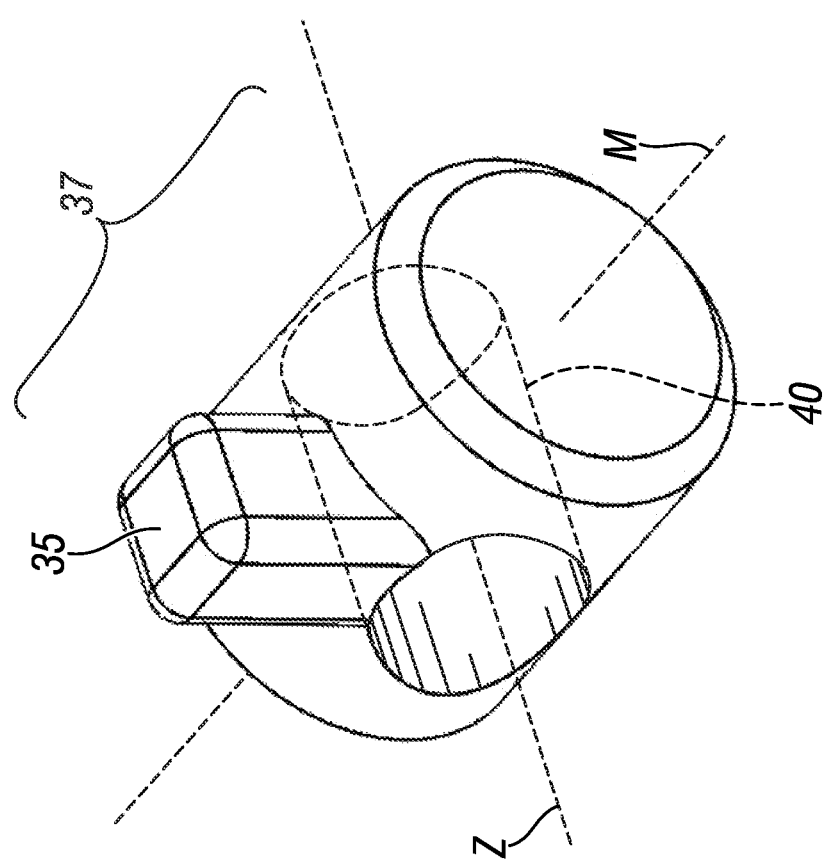

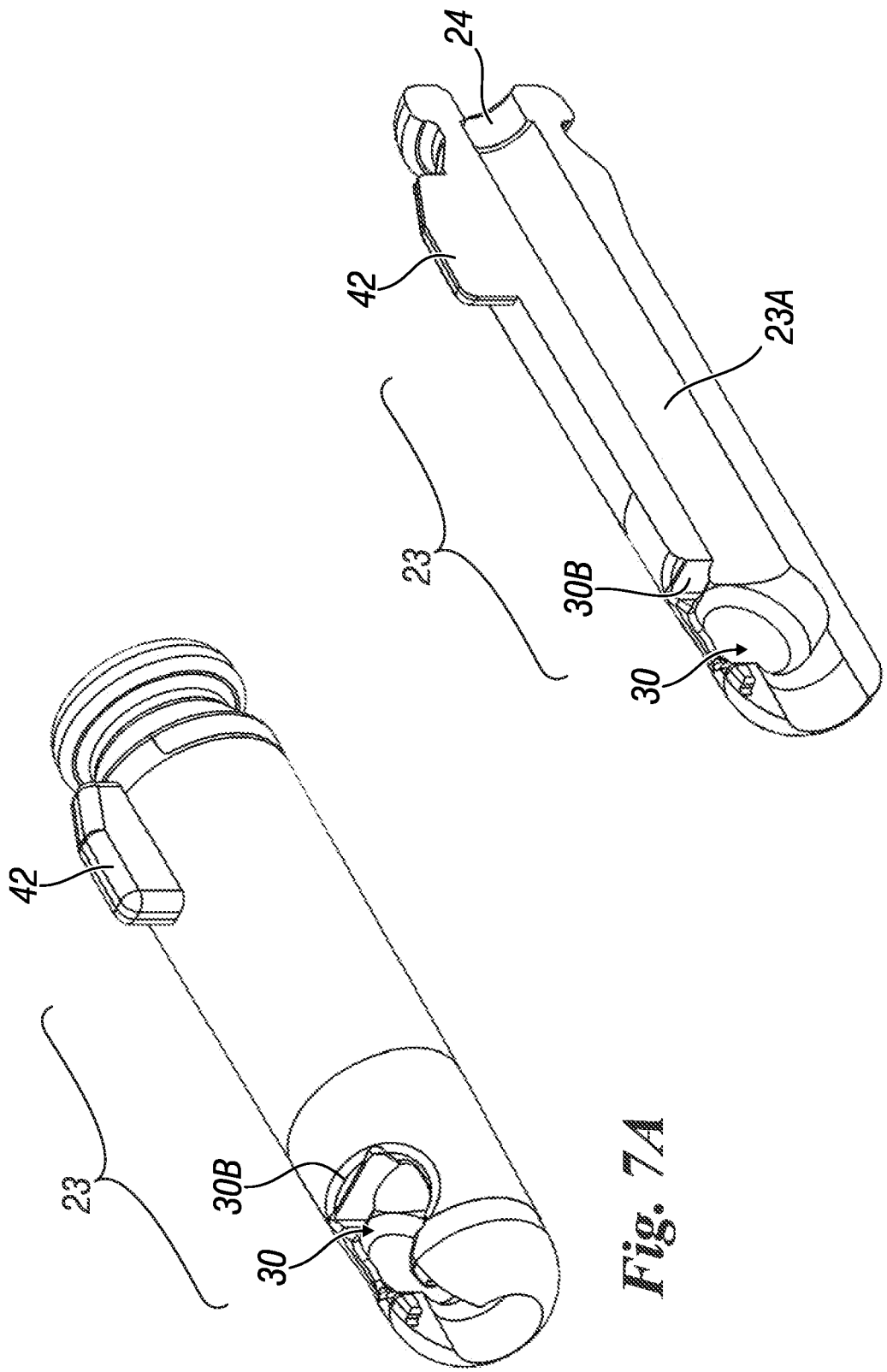

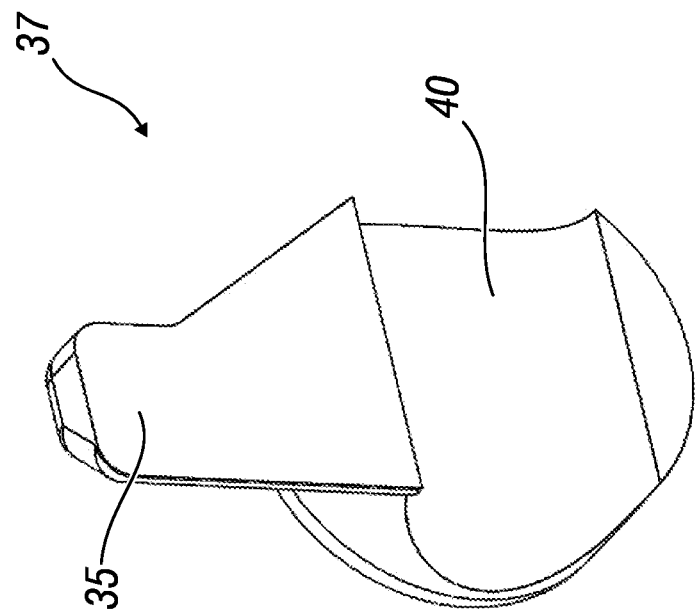
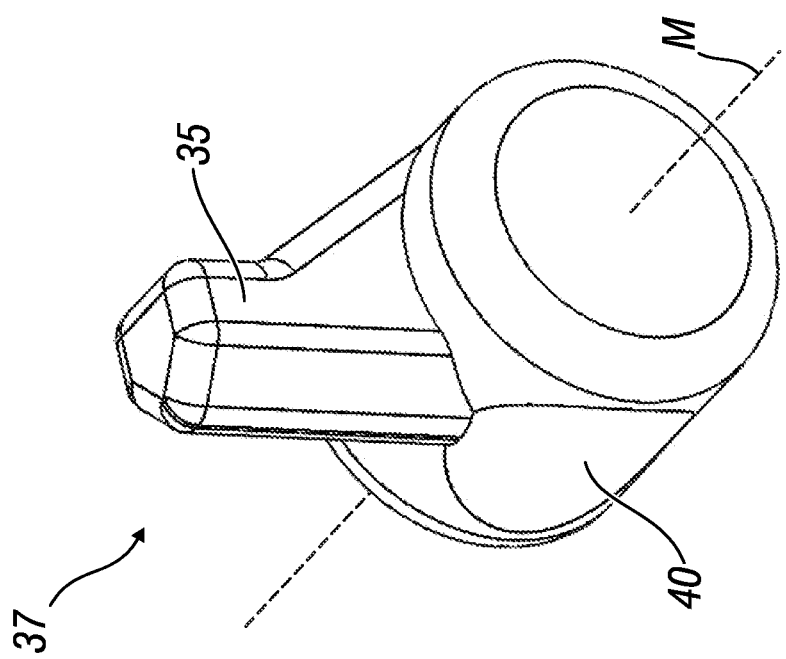

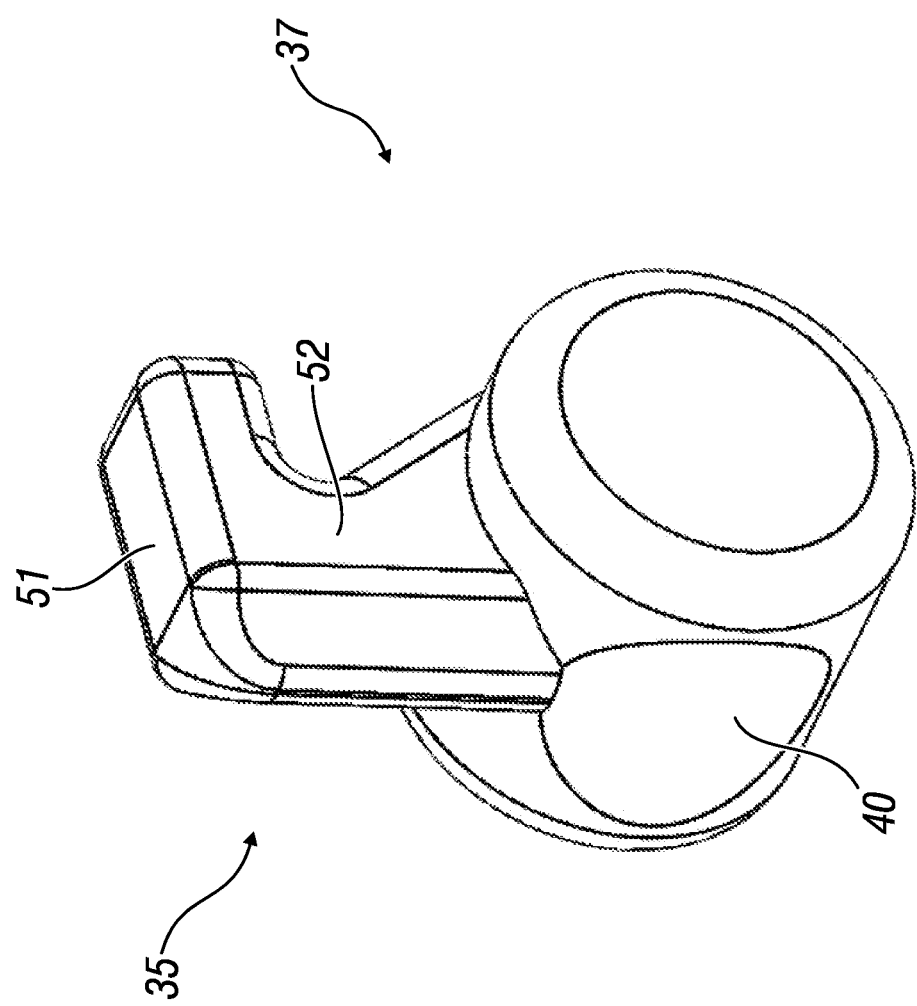

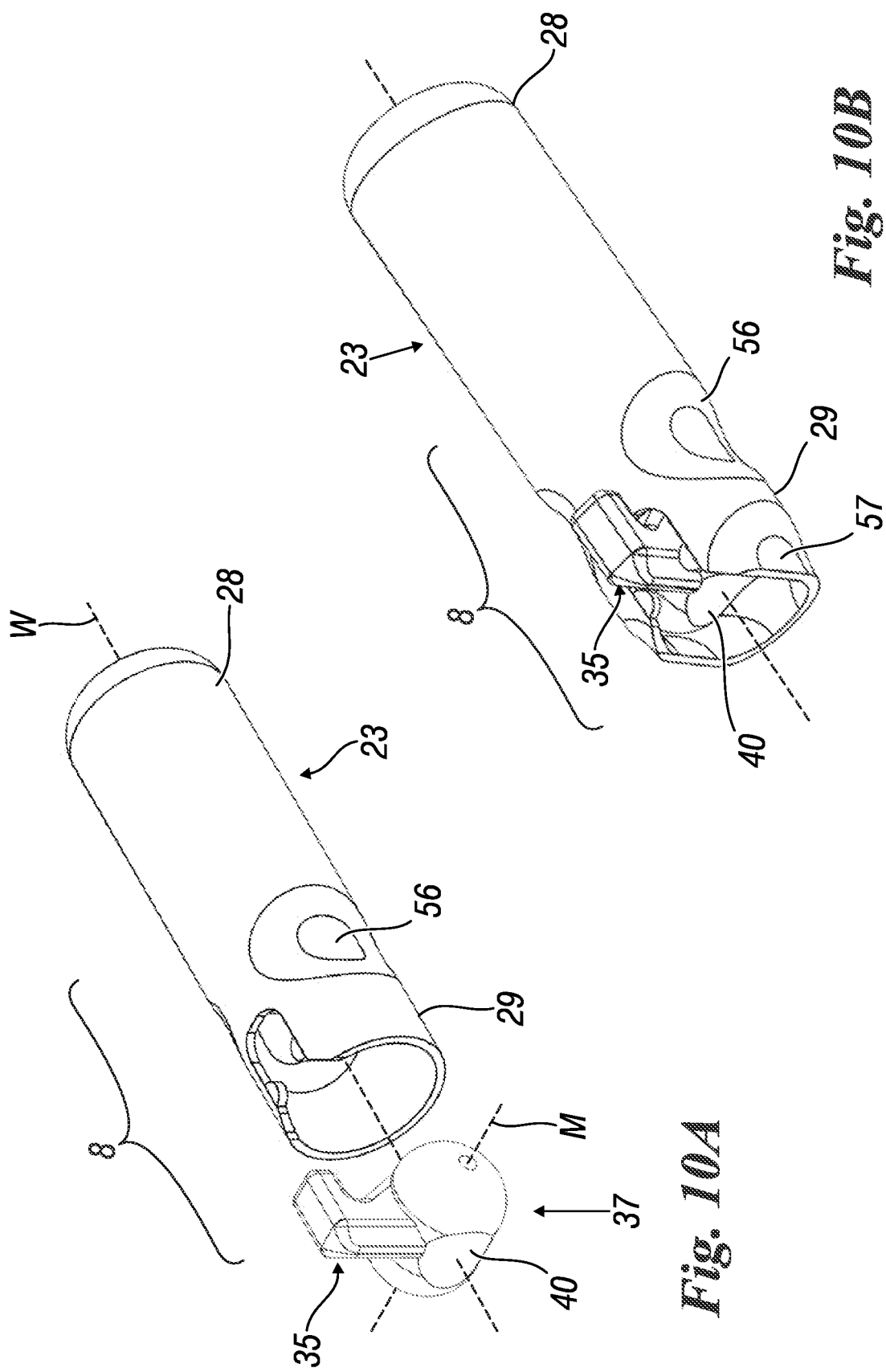

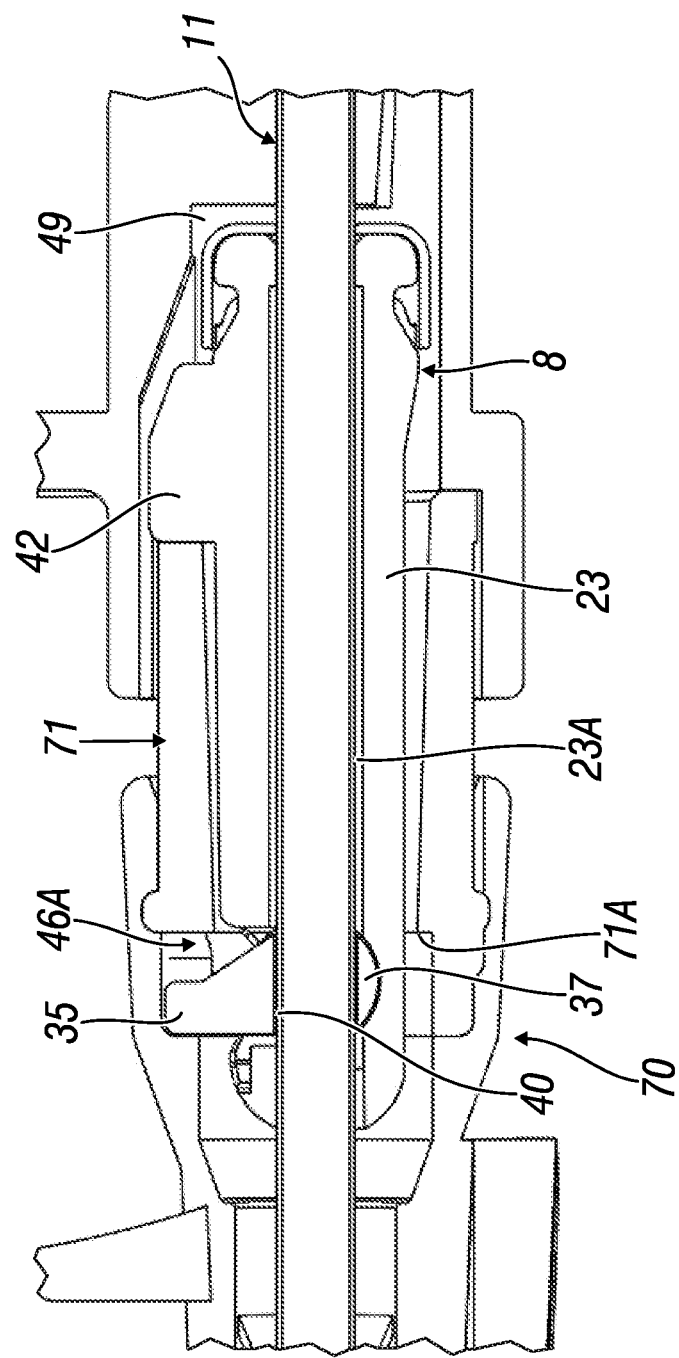

SAFETY CATHETER NEEDLE

CROSS-REFERENCE TO RELATED APPLICATIONS

This application is a 371 of PCT/IB2018/059932, filed Dec. 12, 2018, which claims the benefit of Italian Patent Application No. 102017000145675, filed Dec. 18, 2017.

FIELD OF THE INVENTION

The present invention relates to a safety catheter needle according to the precharacterising clause of the principal claim.

BACKGROUND OF THE INVENTION

As is known, a catheter needle or merely "catheter" is a medical device which enables a catheter of plastics material to be inserted into the peripheral venous system of a patient or into a vein of the latter or into the subcutaneous adipose tissue of the patient in order to be able to administer or extract liquids to or from the latter's body. For the catheter to be inserted into the patient's body provision is made for a metal cannula (with a cutting end projecting from the catheter) inserted within the catheter itself which has the function of inserting the latter into for example a vein of the patient and which is removed by a health professional who performs this insertion operation at the end of the catheter positioning procedure.

With a venous catheter of the type mentioned above there is the problem that when the metal cannula is drawn out from the then positioned catheter the health professional may be accidentally pierced by the cannula; this may happen when the metal cannula is disposed of. This may give rise to problems in that the metal cannula has been contaminated with the patient's body fluids (for example blood) and may be a vehicle for the transmission of infectious diseases.

It is therefore of fundamental importance to provide catheters equipped with safety systems which limit if they do not completely rule out this risk.

Catheters provided with incorporated safety devices protecting health professionals from the risk of accidental punctures and contamination with patients' blood are known on the market. As mentioned, this is with the object of limiting the possibility of contaminating health professionals with patients' biological fluids. These catheters provided with safety devices (which we will refer to as "safety catheters") make it possible to reduce the risk of transmitting infectious diseases which can be carried by blood, such as AIDS, viral hepatitis and the like.

Known safety catheters have incorporated safety devices having different functions and configurations. Some of these, for example, only protect the tip of the cannula once the latter has been drawn out from the catheter, this protection being obtained by enveloping the tip of the cannula in bodies associated with the catheter.

Devices capable of protecting both the tip and the surface of the cannula by means of telescopic systems or sliding shells activated manually by the health professional after the cannula has been drawn out from the catheter are in particular known; such are for example described in U.S. Pat. Nos. 4,747,831 and 6,436,070. These devices are referred to as safety catheters of the active type.

It is known however that systems provided with resilient means for immobilising the cannula can have disadvantages due to the excessive speed with which the cannula retracts, such as for example giving rise to small splashes of body fluid outside the body containing the tip, and high noise and vibration at the end of the travel of the resilient element immobilising the tip.

Other devices which operate in passive mode which snap to resiliently immobilise the cannula within the protective body, as described in US2016220791, are known.

The systems for enveloping only the tip after the cannula has been drawn out from the catheter may be either housed within a catheter holder or outside it. When removed outside the catheter holder the systems protecting only the tip often have lateral or frontal openings such that in principle they do not prevent small drops of patients' body fluid from emerging, and this might give rise to problems for the health professional.

In addition to this, if the cannula is deformed, it is not possible to rule out a priori the possibility that the contaminated tip may come in contact with the health professional through openings present in the protecting body.

Safety catheters provided with devices capable of preventing a health professional from coming into contact with the tip of the cannula after it has been drawn out from the catheter and operating through a moving rotating element between the catheter holder which houses the aforesaid tip after it has been drawn out from the catheter are known. For example, EP2211942 describes a protection system associated with the catheter holder and comprising a moving element which through rotation in a chamber of the catheter holder (or an adapter associated therewith) is capable of receiving the tip of the cannula before the latter projects from the catheter holder itself. Rotation takes place because of the interference between a bevel in the cannula close to its tip and said moving element during the stage in which the cannula is removed from the catheter holder.

This solution is relatively difficult and costly to construct in that it requires a catheter holder of very different shape from that of normal catheter holders already present in the state of the art and specifically provided with a special specific seat for the above-mentioned moving element. As an alternative an adapter must be made for this element which has to be attached to the catheter holder.

It is also required that the moving element should be of such a shape as to ensure that it couples with the tip of the cannula and this makes it necessary to manufacture the parts (at least the moving element) with very small construction tolerances, which is in itself very difficult. Small offsets between the catheter holder and the moving element or even small variations in construction may result in incorrect movement of the moving element with consequent malfunction of the protection device described in the prior document.

In addition to this, this moving element does not ensure that body fluids (for example blood) associated with the cannula are contained, with the consequent possibility that they may be lost, with obvious hazards and disadvantages for both any health professionals and persons who might come into contact with it.

U.S. Pat. No. 5,300,045 describes a catheter needle according to the precharacterising clause of claim 1.

US 2008/065015, WO 2012/016660 and EP 1 920 796 describe safety devices which prevent contact with the tip of a cannula after use.

These devices have protection members provided with a rotating element or part capable of being located in front of the tip of the cannula after this has entered such protection component.

WO 00/06226 describes a different safety device capable of preventing contact with the tip of a catheter after use.

SUMMARY OF THE INVENTION

The object of the present invention is to provide a safety catheter needle (or merely "safety catheter") of the above-mentioned type which is improved in comparison with similar known solutions.

In particular the object of the present invention is that of providing a catheter of the type mentioned which offers improved safety not only with respect to the fact that the tip of the cannula cannot come into contact with a health professional, but also in that there is a small possibility that body fluids may emerge from the protective element and come into contact with the health professional.

Another object of the present invention is that of providing a safety catheter of the type mentioned which operates in wholly passive mode or without the health professional having to act in order to achieve protection of the tip of the cannula by acting on the latter or on members associated with it.

Another object is that of providing a safety catheter of the type mentioned in which the tip of the cannula is absolutely inaccessible to an operator after it has been drawn out from the catheter holder.

Another object is to provide a safety catheter of the above-mentioned type which does not lose its protection characteristics over time, said characteristics remaining unchanged even after different periods of time after production of the catheter.

Another object is that of providing a safety catheter which has a small number of components and is simple to manufacture and assemble, such as to have high reliability in use and low cost.

These and other objects which will be apparent to those skilled in the art will be accomplished through a venous catheter according to claim 1.

BRIEF DESCRIPTION OF THE DRAWINGS

For a better understanding of the present invention there are attached purely by way of example and without limitation the following drawings, in which:

FIGS. 5a and 5b show assembled perspective views of the protection device in FIG. 4 during different stages of use;

FIGS. 6a and 6b show perspective views of the individual components of the protection device in FIG. 4;

FIGS. 7a-7b show a perspective view and a longitudinal cross-section respectively of a variant of a first component of the device in FIG. 4;

FIGS. 8a and 8b show a perspective view and a longitudinal perspective cross-section respectively of a variant of a second component of the device in FIG. 4;

FIG. 9 shows a perspective view of another variant of the second component of the device in FIG. 4;

FIGS. 10a and 10b show perspective views, in exploded view and before and after completion respectively, of a variant of the first component of the device in FIG. 4;

FIGS. 15a, 15b, 15c show portions of the catheter in FIG. 11 during different stages of use.

DETAILED DESCRIPTION OF THE INVENTION

Figure 1:
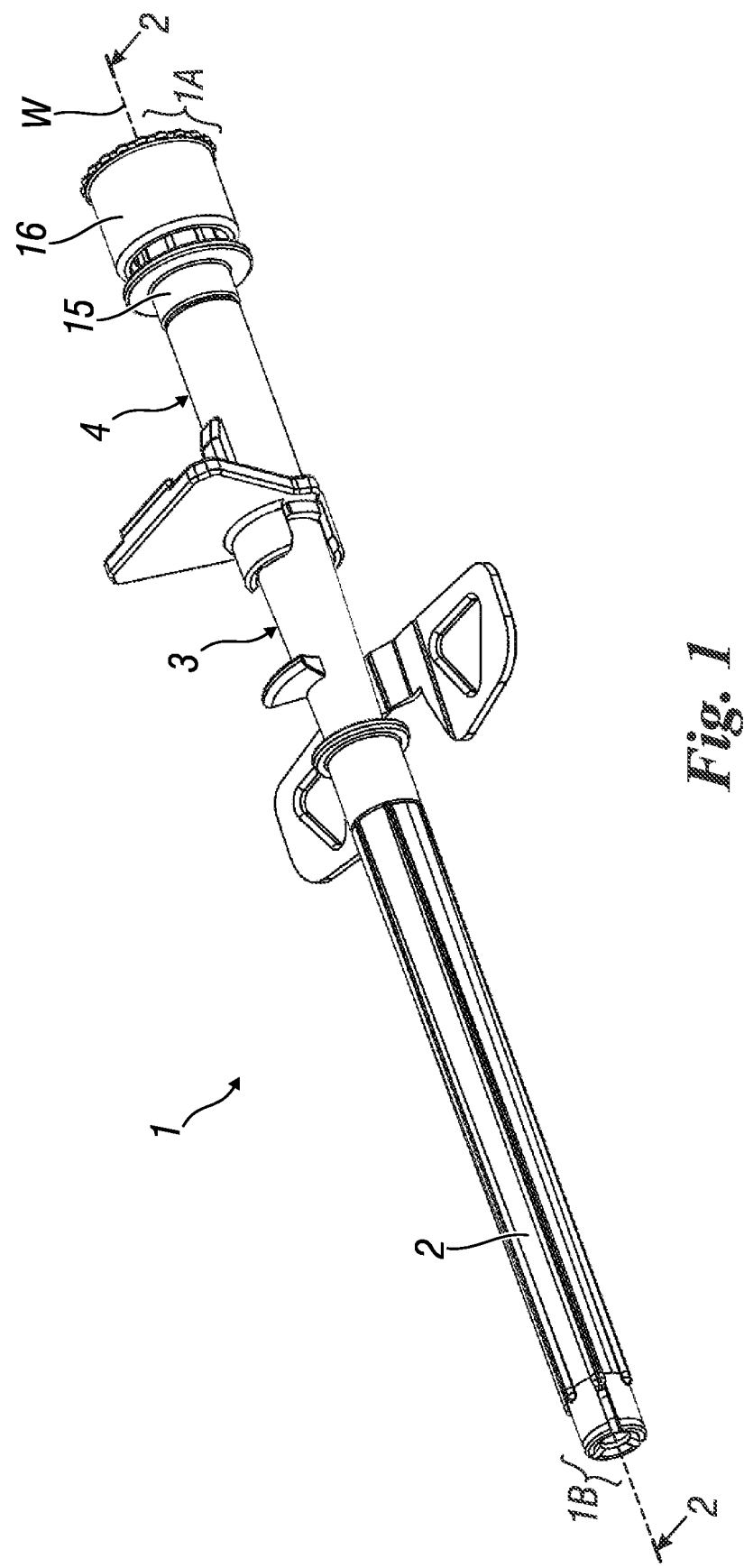
FIG. 1 shows a perspective view of a safety catheter according to the present invention.
Figure 2:
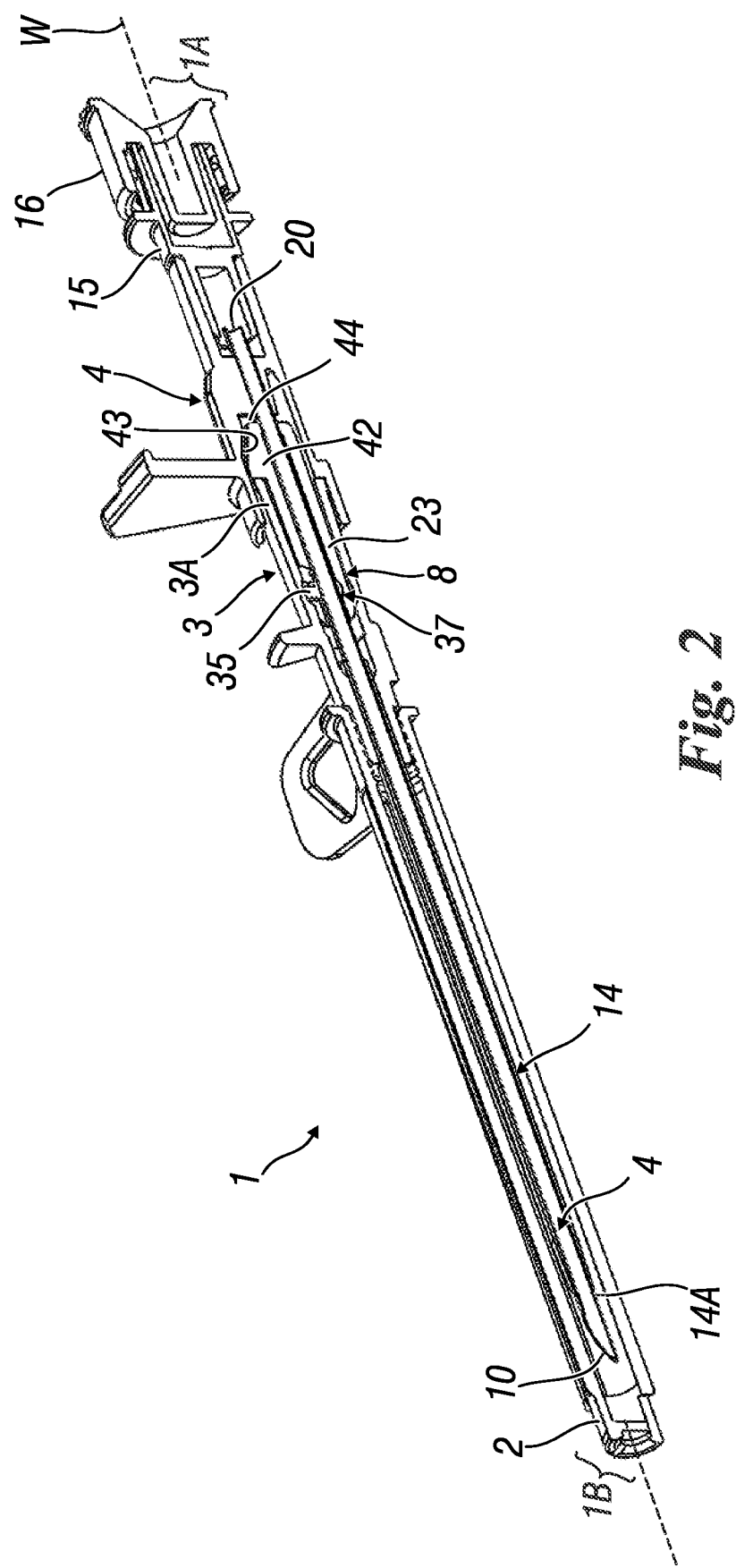
FIG. 2 shows a cross-section along the line 2-2 in FIG. 1.

With reference to FIGS. 1-10, these show a safety catheter needle (or "safety catheter") according to the invention; the safety catheter is indicated as a whole by reference number 1. This safety catheter comprises as a whole (see FIGS. 1-3), a protection element or protector 2 which when associated with safety catheter 1 is made of one piece in a known way with catheter holder 3 which in turn is removably attached to a cannula holder 4. The cannula holder comprises a normal chamber for the backflow of body fluid (for example blood); a safety device 8 is associated with catheter holder 3 and is capable of containing a tip 10 of a cannula 11 after the latter has been drawn out from the catheter holder after catheter 1 has been used.

Figure 3:
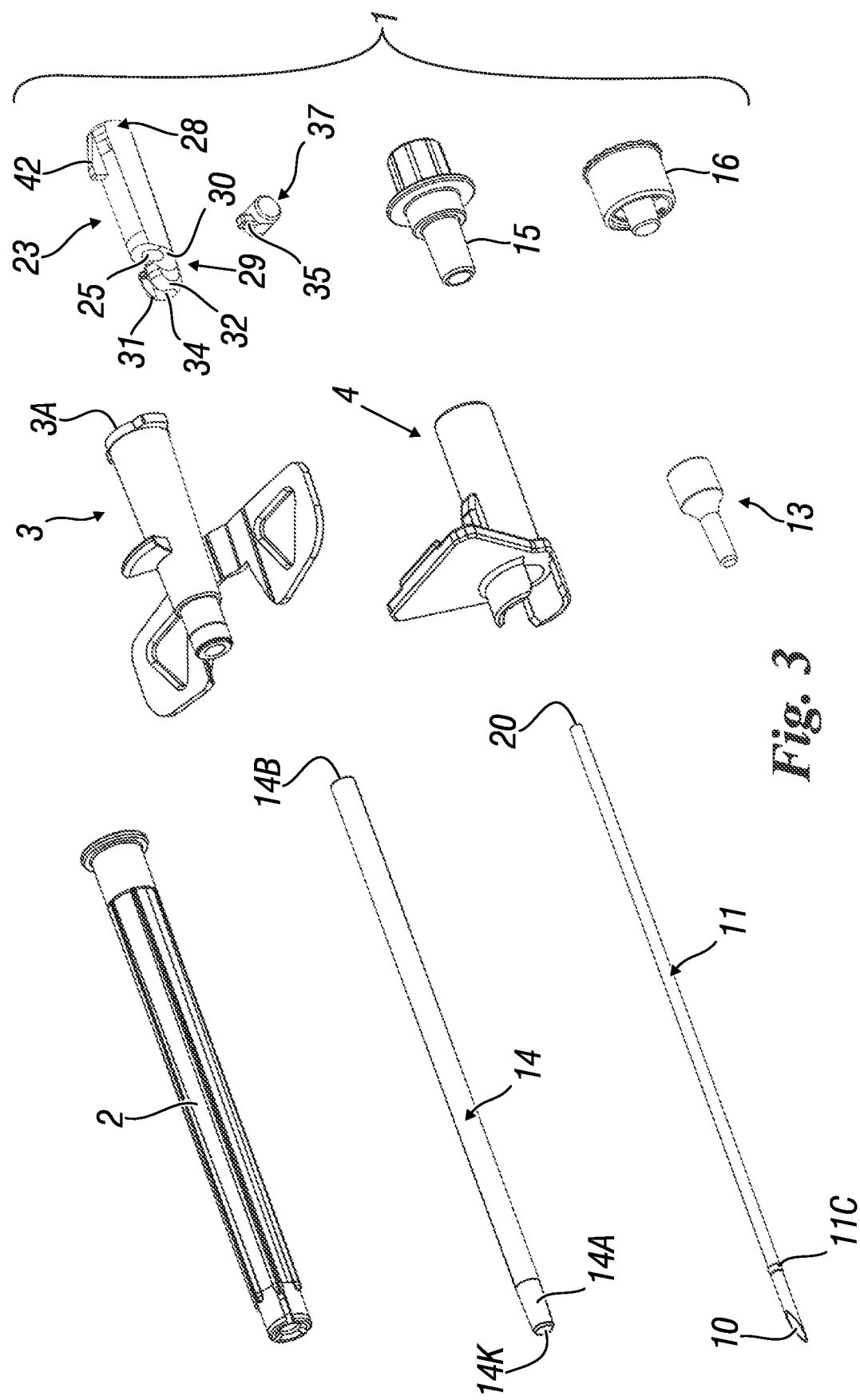
FIG. 3 shows an exploded perspective view of the catheter in FIG. 1 in which all the components of the safety catheter are shown.

Provision is also made in catheter holder 3 for a catheter immobilising insert 13 (see FIG. 3). Cannula holder 4 is also preferably associated with a normal ventilation connection having a hydrophobic filter 15 (or other equivalent system which is in itself known) and a Luer Lock cap 16, which is in itself known.

Cannula 11 has a variation in cross-section, for example a bevel 11C close to its tip or distal extremity 10.

The proximal extremity 20 of cannula 11 is internally fixed to cannula holder 4.

It will be noted that the terms "proximal" and "distal" are used in relation to the positions of cannula 11 with respect to cannula holder 4 or, better, Luer lock cap 16 (or extremity 1A of safety catheter 1 opposite extremity 1B where tip 10 of cannula 11 is present); every further mention of "proximal" or "distal", including with reference to other components of safety catheter 1, will relate to the latter.

Metal cannula 11 has a distal extremity or tip of cannula 10 constructed, for example by means of a cut on an inclined plane with respect to the longitudinal axis W of the cannula (and the entire safety cannula 1), so that it is cutting. This cannula 11 is capable of permitting a catheter 14 to be inserted into a vein, an artery or the adipose tissue of a patient, an operation normally performed by a health professional. For this purpose catheter 14 has a longitudinal through hole 14K; the distal extremity or tip 10 of cannula 11 projects from a distal extremity 14A of catheter 14 before and during the aforesaid operation.

Catheter 14 has a proximal extremity 14B which in a known way is of one piece with catheter-immobilising insert 13.

As mentioned, the catheter holder comprises protection and safety device 8 which is capable of receiving and retaining within it the distal extremity or tip 10 of cannula 11 after catheter 14 has been inserted into the body of a patient and this cannula has been drawn out from the catheter itself.

More particularly, safety device 8 is of the passive type and comprises a containment body 23 (or "first body" or "principal body") having a through longitudinal cavity 23A (located along the W axis) with a proximal opening or hole 24 in a proximal portion 28 of body 23 and a distal opening 25 in a distal portion 29 of the body itself (which also represents the distal extremity of protection device 8). Hole or opening 24 has dimensions which are smaller than the dimensions of bevel 11C (and will also be described below as a small hole 24).

Containment body 23 can contain the distal extremity or tip 10 of cannula 11 after said cannula has been drawn out from catheter 14 in order to protect a health professional who has performed the aforesaid extraction operation.

At distal extremity 25 containment body has a cavity 30 which is open on three sides (30A, 30B, 30C) adjacent to arms 31 and 32 having three ends 33 facing distal opening 25 that are resiliently drawn together. These arms 31 and 32 bound a channel 34 capable of receiving an eccentric lateral projection 35 of a moving body 37 (or second body of device 8) substantially of a barrel or cylindrical shape held in such a way that it can rotate within above-mentioned cavity 30.

In particular, rotating moving body 37 (which is cylindrical or in any event of a shape approximating to a solid of revolution) has a longitudinal axis and rotation axis M located at right angles to axis W and can rotate within cavity 30 when eccentric lateral projection 35 experiences a force directed along the W axis in the direction of distal extremity 29 of containment body 23 (as will be described below).

Arms 31 and 32, which are located next to distal portion 29, have projections 38 facing each other on which is supported lateral projection 35 of rotating moving body 37 when the latter is in the first working position in which cannula 4 passes through it.

Rotating movable body 37 in fact has a through hole 40, having an axis Z at right angles to the M axis (and therefore capable of overlapping the W axis), and this hole 40 is capable of containing cannula 11 in passing mode when the latter is within catheter 14 or is outside protection device 8. In this case hole 40 has an axis Z substantially coinciding with above-mentioned W axis and specifically contains said catheter with through cavity 23A of principal body 23. This hole 40 is thus coaxial with cavity 23A in body 23.

It will be noted that the terms "substantially coinciding with" or "substantially capable of being overlapped with" mean that the Z axis may be precisely overlapped with and coincide with the W axis, but also that this Z axis may be slightly inclined with respect to the W axis. This may for example arise because of the fact that the rotating movable body is slightly rotated within cavity 30 and the edge of hole 40 bears against cannula 11 when this cannula is inserted in said hole.

In addition to this, body 23 or first body of protection and safety device 8 has a fin or projection 42 which when the safety catheter is in use (or catheter 14 is inserted into the patient) is capable of acting together with a wall 43 of a cavity 44 within cannula holder 4 to ensure correct alignment with such cannula holder. At the same time projection 42 bears on a proximal extremity 3A of catheter holder 3 (see FIGS. 2, 4a and 4b) and acts as an immobilising agent to prevent device 8 from being excessively inserted within such cannula holder, with a corresponding increase in the extraction force, when safety catheter 1 is being assembled.

It should be noted that both translational and rotational alignment with cannula holder 4 is essential for correctly positioning tip 10 of cannula 11 with respect to a normal taper which is provided on catheter and to orientate the sharp part of the aforesaid cannula tip in such a way that the apex of the tip faces the surface of the injection site.

Figure 4A:
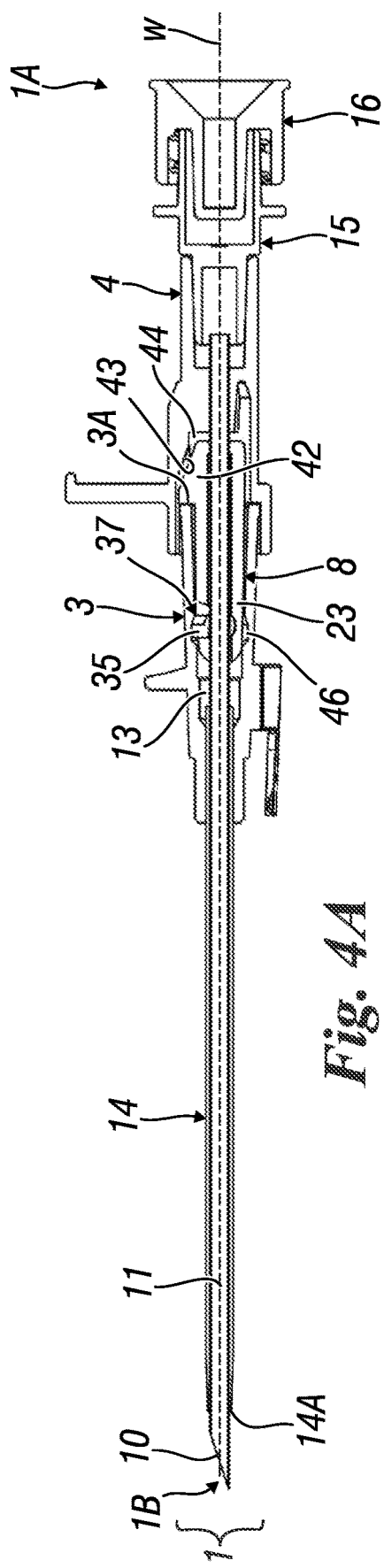
FIGS. 4a-4d show cross-sectional views of a safety catheter according to the invention (FIG. 4a) and various stages in the extraction of a cannula from a catheter holder, with the intervention of a protection device according to one embodiment of the invention.
Figure 4B:
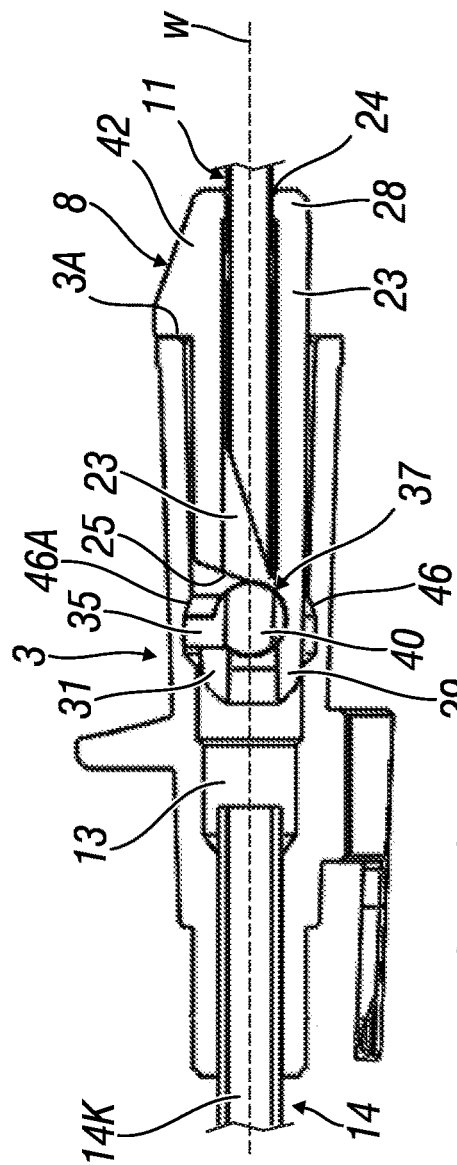
Figure 4C:
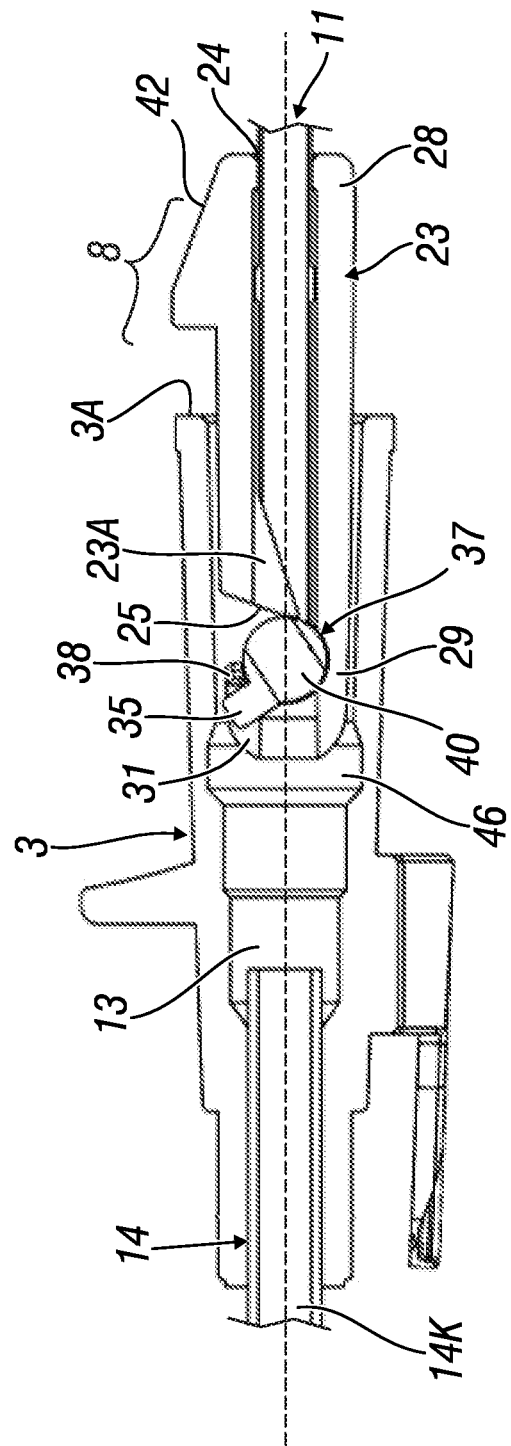
Figure 4D:
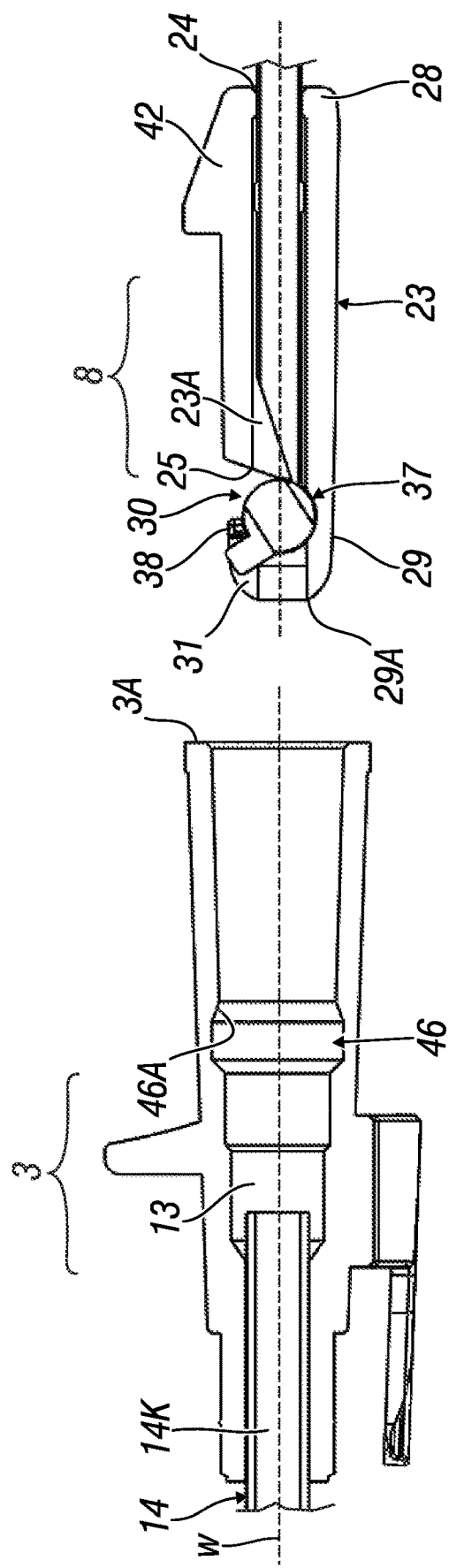
Figure 5A:
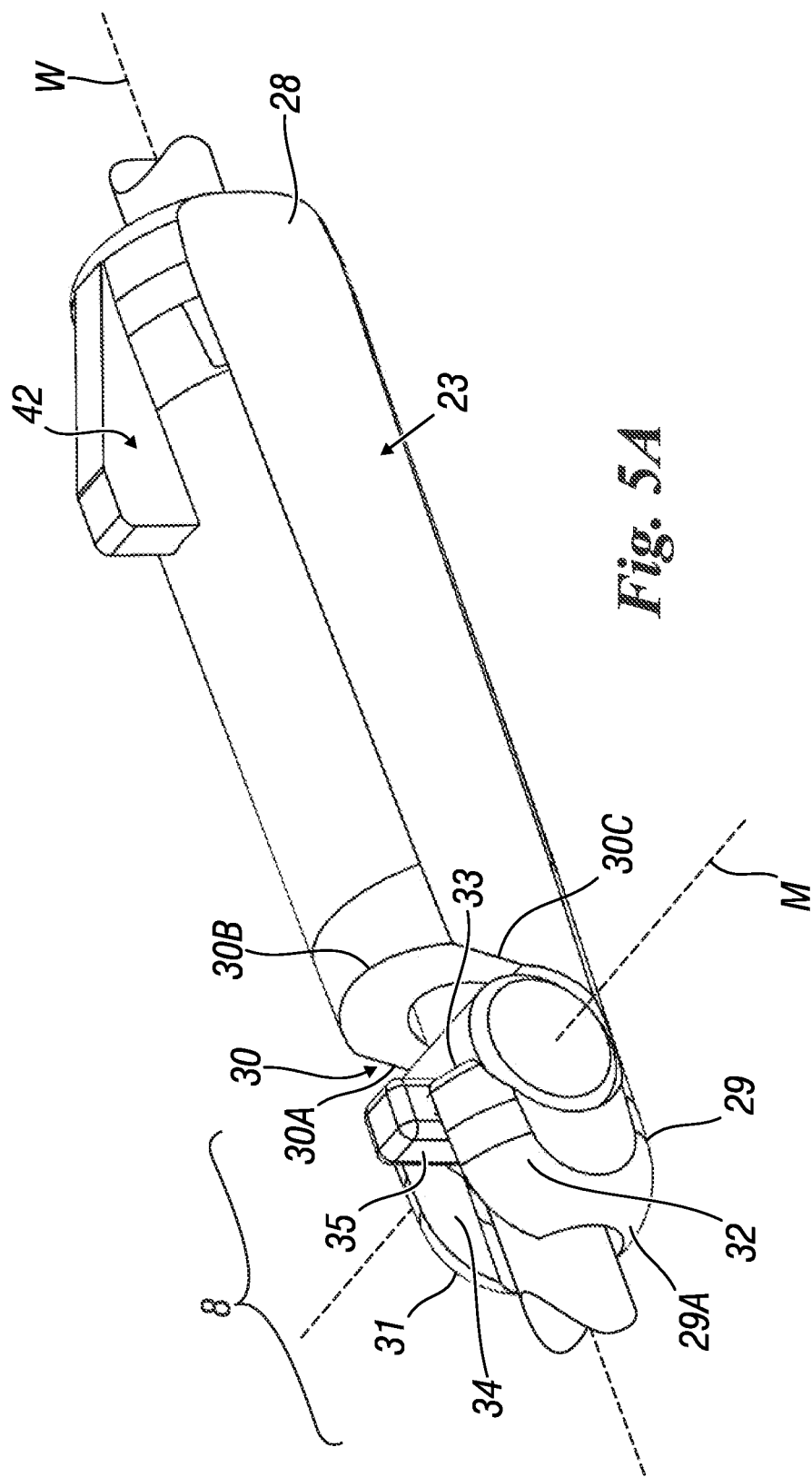
Figure 11:
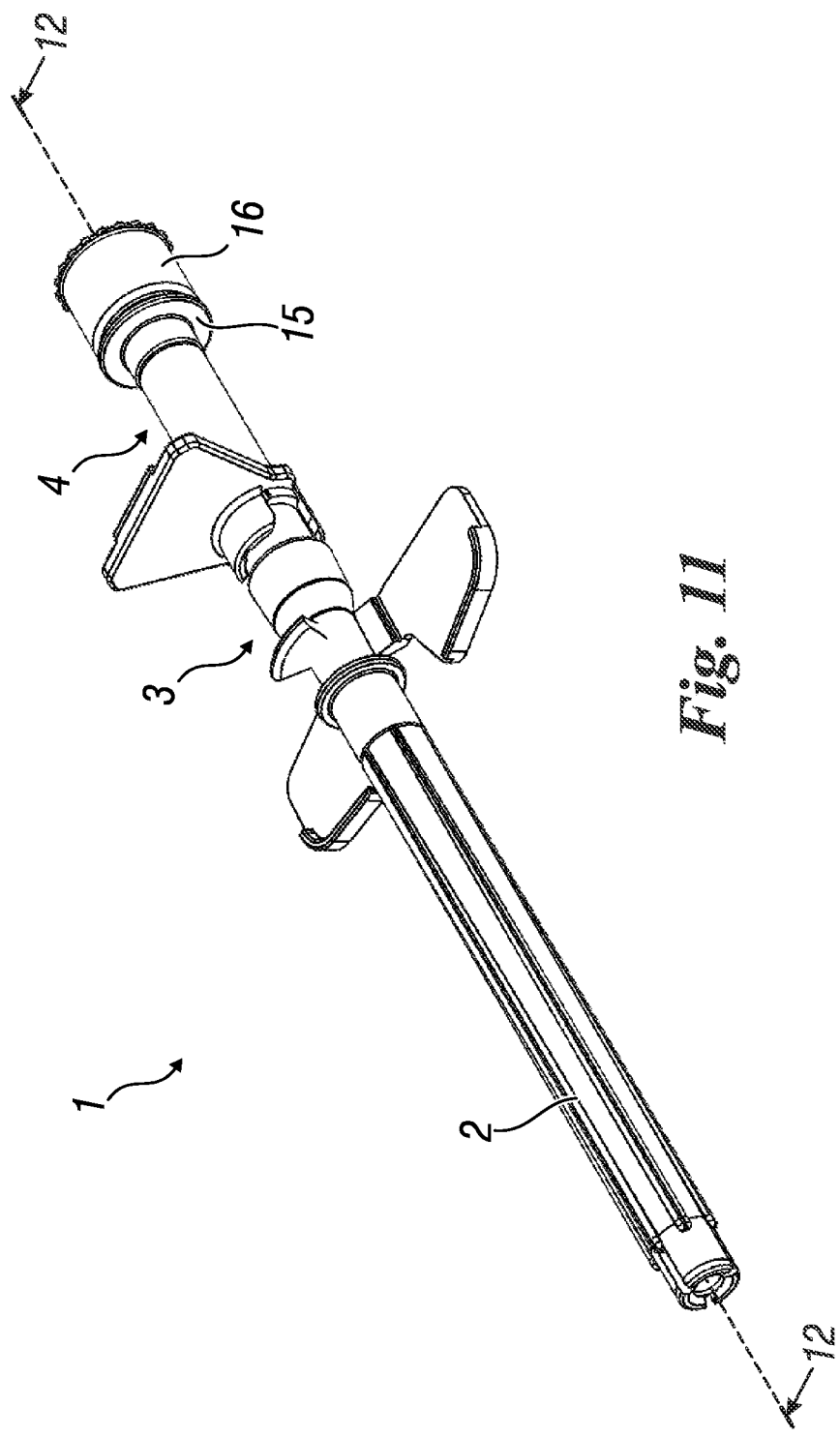
FIG. 11 shows a perspective view of a variant of a safety catheter according to the invention.
Figure 12:
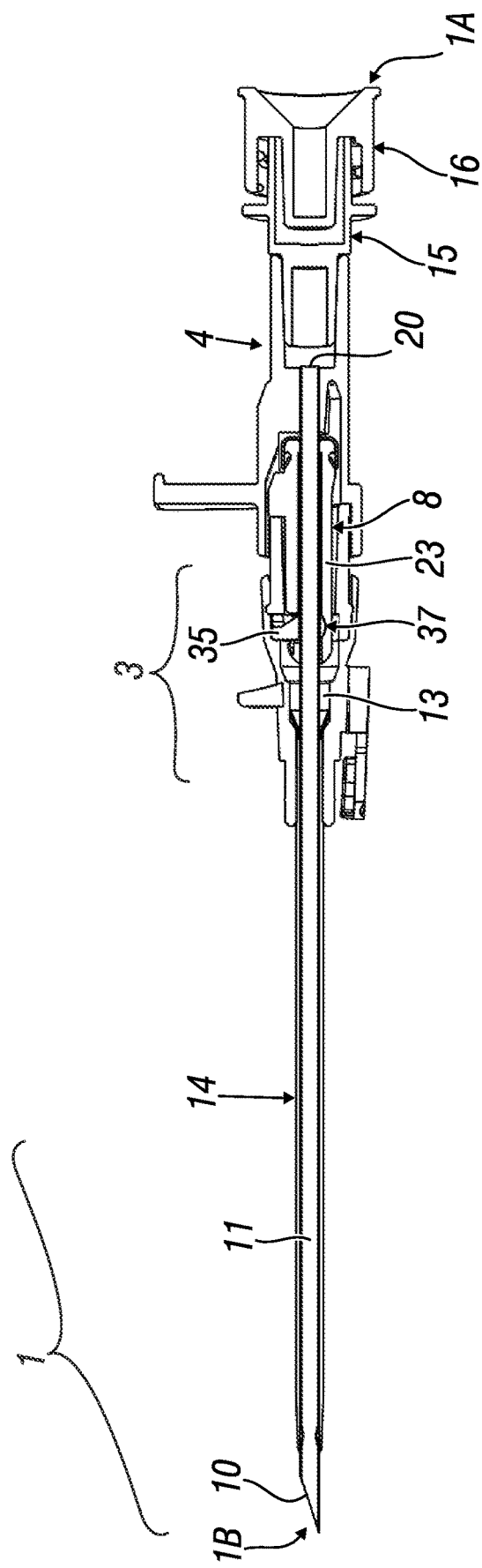
FIG. 12 shows a cross-section along the line 12-12 in FIG. 11, with part of the catheter not shown for greater clarity.
Figure 13:
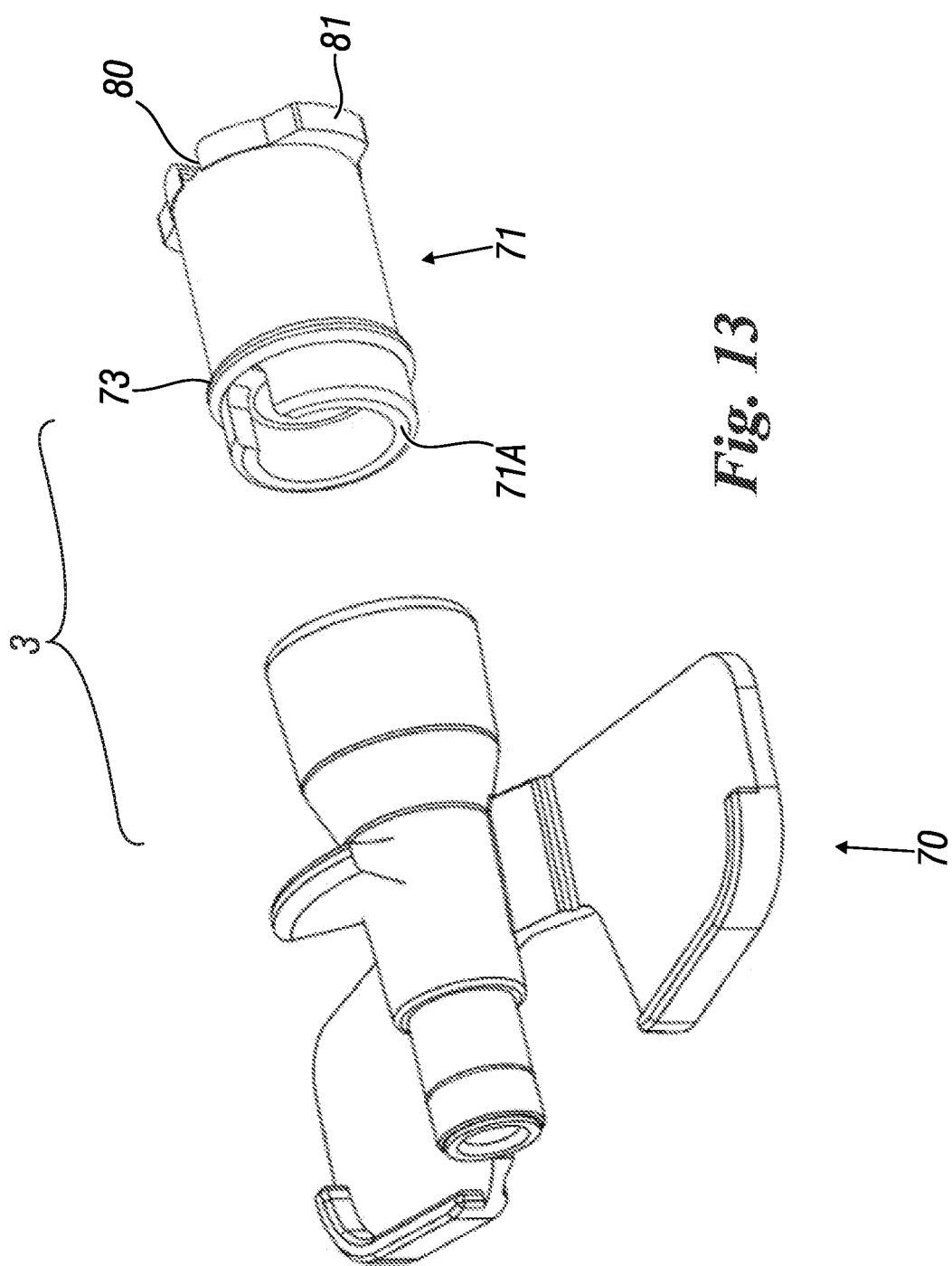
FIG. 13 shows a perspective exploded view of a detail of a catheter holder according to a variant of the invention shown in FIG. 11.
Figure 14:
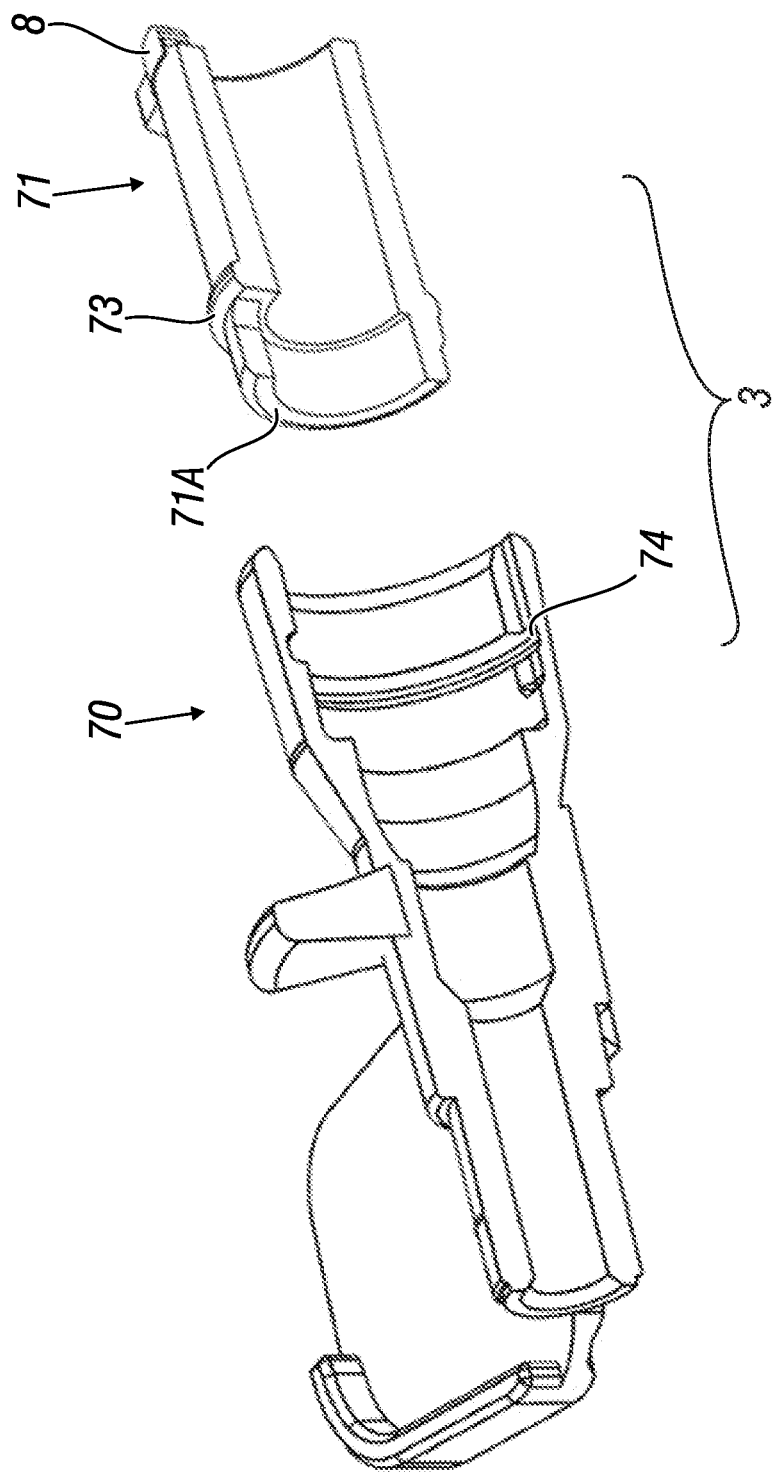
FIG. 14 shows the catheter holder in FIG. 13 in exploded perspective view and longitudinal cross-section.

Catheter holder 3 has internally an enlarged part 46 which when the safety catheter is in the position of use and catheter 14 and cannula 11 are inserted into a patient is capable of containing lateral projection 35 of rotating moving body or second body 37 of device 8 (see FIGS. 4a and 4b). This enlarged part 46 has a proximal step 46A capable of interacting or acting directly together with projection 35 of body 37 when cannula 11 is drawn out from catheter 14. Following this interaction body 37 rotates in cavity 30 and this projection moves between arms 31 and 32 into channel 34 towards distal extremity 29A of distal portion 29 of body 23.

During a stage in which cannula 11 is being drawn out from catheter 14 bevel 11C constructed close to tip 10 of cannula 11 interferes with (small) hole 24 made in the principal body or containment body 23. The interference causes principal body 23 of safety device 8 to move back with respect to catheter holder 3. Moving body or second body 37 borne by the principal body and rotating therein interferes through projection 35 with step 46A made in enlarged part 46 of catheter holder 3. As principal body is drawn back this projection engages step 46A and thus causes rotation of moving body 37 which can rotate because tip 10 of cannula 11 is fully inserted within cavity 23A provided in principal body 23. Hole 40 of rotating moving body 37 is free from the cannula, while tip 10 thereof, which has been drawn out from the catheter, is wholly within cavity or hole 23A. Arms 31, 32 and their resiliently movable projections 38 prevent reversal of the rotation of cylindrical body 37 and thus constitute an obstacle to realignment between hole 40 and cavity 23A for the passage of cannula 11 preventing tip 10 of the cannula from being exposed from safety device 8 through distal extremity 29 of device 8.

This device is made of plastics material (preferably self-lubricating low-friction plastics) having sufficient strength not to be deformed or altered by tip 10 of the cannula and therefore capable of preventing it from emerging, even in the event of accidental impact.

Figure 15B:
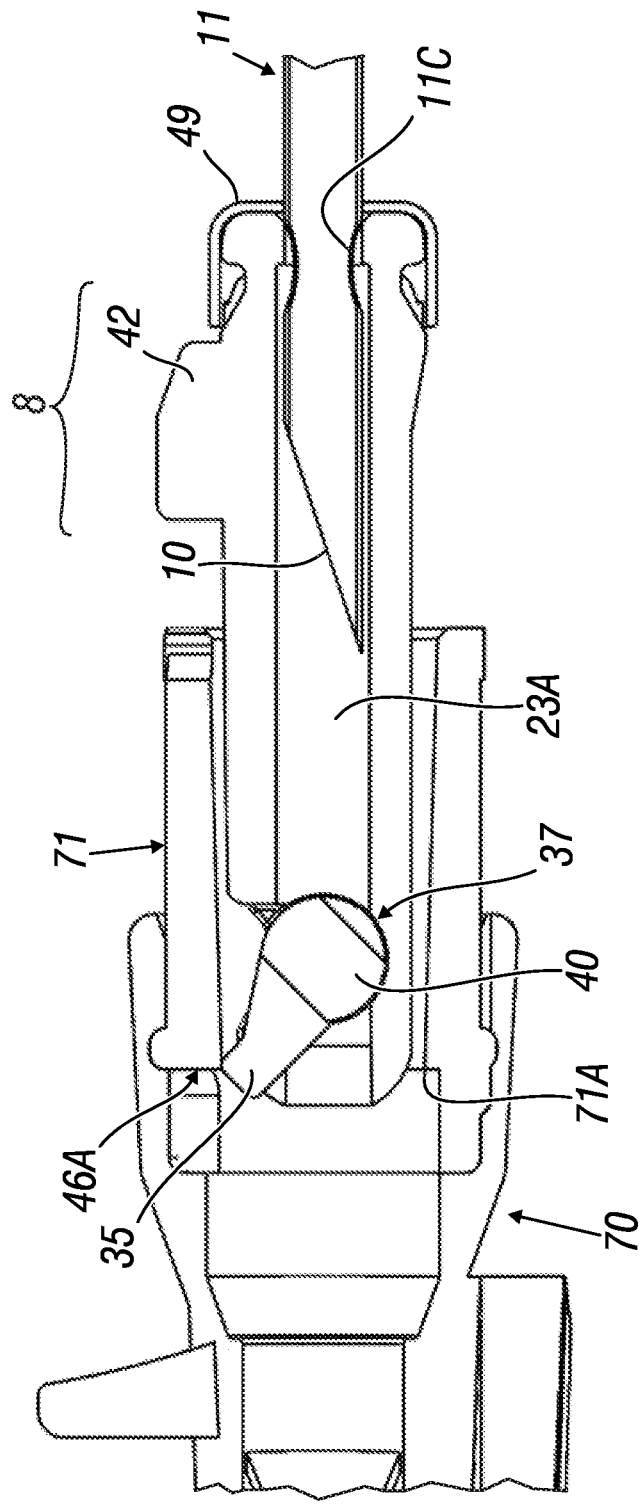
Figure 15C:
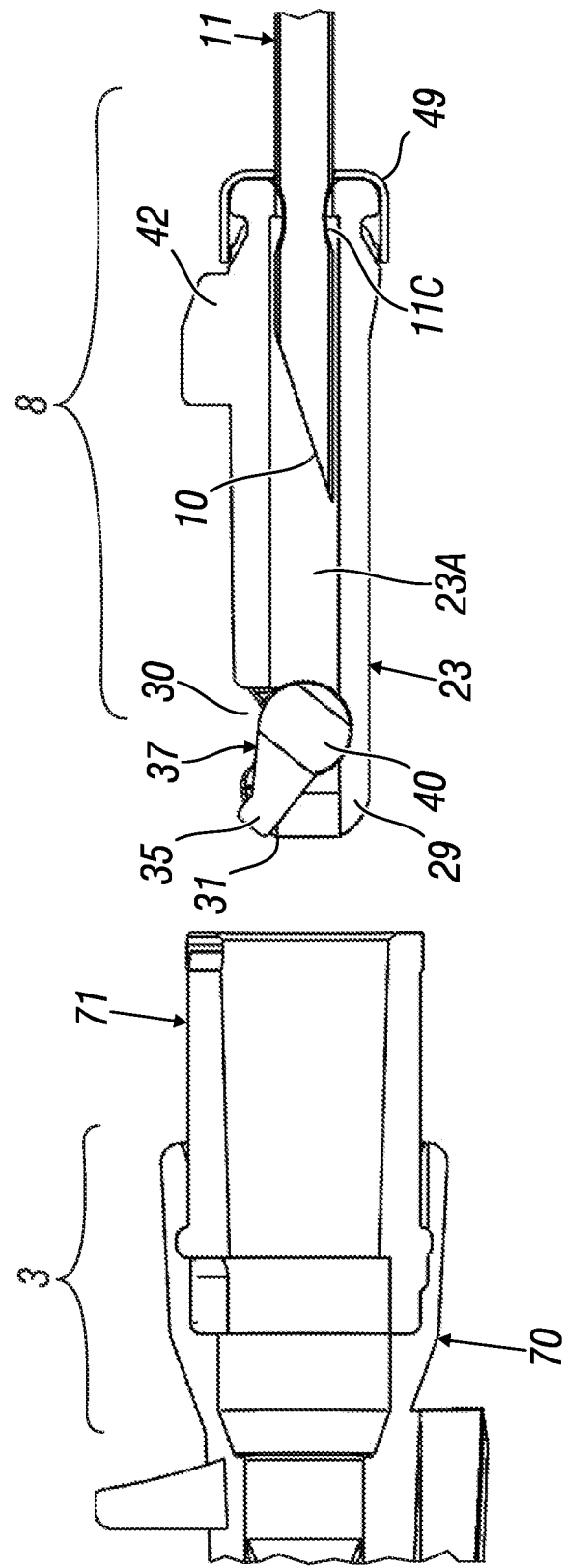

The (calibrated) hole 24 in cavity 23A present in principal body 23 of the safety device can advantageously be reinforced by a metal annular element or ring 49 which is co-moulded and assembled therewith (see FIGS. 15a-c). This metal ring ensures greater interference between bevel 11C of cannula 11 and calibrated hole 24 so as to prevent tip 10 of the cannula from emerging therefrom.

In an alternative embodiment of device 8 and in particular of cylindrical body 37 (FIGS. 8a and 8b), projection 35 which causes such cylindrical body to rotate by acting together with step 46A of the catheter holder is of an increased length in comparison with that of the solution in the figures above such as to cause greater angular rotation and ensure greater safety in the action of device 8. In another possible embodiment (see FIG. 9) the angle of rotation of rotating cylindrical body 37 is further increased through a projection 35 in the shape of an upside-down L comprising horizontal portion 51 and a vertical portion 52; this solution further delays the moment when such projection 35 engages step 46A.

In a further alternative embodiment of the invention (see FIGS. 7a and 7b), principal body 23 of safety device 8 is made as a cylindrical member in which cavity 30 for rotating body 37 opens on only one side 30B in such principal body (and, obviously, towards channel 34); this solution enables said rotating cylindrical body 37 to be inserted into cavity 30 from that side so that it is immobilised therein, while allowing it to rotate (see FIGS. 7a and 7b).

In a further embodiment (see FIGS. 10a and 10b), principal body 23 is made of metal or from a metal sheet. This ensures correct interference between hole 24 of through cavity 23 and bevel 11C in cannula 11 without having to resort to an additional metal immobilising ring (with consequent advantages during the assembly stage and a smaller number of components). In this latter embodiment one possible way of obtaining safety device 8 comprises starting from a tubular metal structure, closed by an end member in which there is made (calibrated) hole or opening 24 capable of interfering with bevel 11C and bringing about successive resilient deformations 56 and 57 (deformation 57 corresponding to distal portion 29) so as to lock translation movement of cylindrical body 37 along the W axis without blocking its rotation. This body 37 is inserted axially into body 23 from distal portion shaped, before it undergoes resilient deformation (57), in the form of a cylindrical tube (see FIG. 10a). Final resilient deformation 57 immobilises such cylindrical rotating body 37 within cavity 30 created between deformations 56 and 57 (FIG. 10b).

In a further embodiment of the invention, shown in FIGS. 11-15c (where parts corresponding to those in the figures already described are indicated using the same reference numbers), catheter holder 3 comprises two components 70 and 71 assembled together by means of an interference fit (or by other suitably equivalent means of the ultrasound welding or adhesive bonding type). This makes it possible to obtain a marked step 46A between said components (see FIGS. 15a and 15b) through which a greater angle of rotation of cylindrical body 37 can be obtained when cannula 11 is separated from catheter 14. This step is defined by the free extremity 71A of component 71.

Components 70 and 71 are joined together by the (snap) insertion of a collar 73 of component 71 into an annular recess 74 in component 70. Obviously these components may be joined together using other known means, such as adhesive bonding or ultrasound welding.

Advantageously, component 71 (the proximal component of catheter holder 3 attached to distal component 70) may have a recess 80 on an annular flanged edge 81 capable of orientating safety device 8 in an optimum way with respect to catheter holder 3 so that tip 10 of the cannula is in the correct position as described above.

Various embodiments of the invention have been described. Yet more are possible in the light of the above description and within the scope of the invention as defined by the following claims.

The invention claimed is:

1. A safety catheter needle comprising:
   a cannula having a longitudinal axis (W) which is removably inserted in a catheter and associated with a cannula holder, said catheter being associated with a catheter holder which is in turn removably attached to said cannula holder,
   the cannula having a proximal extremity attached to the cannula holder and a distal extremity or tip of the cannula close to the distal extremity of such cannula having a deformed part,
   the catheter holder comprising a protection device configured to move within the catheter holder when the cannula is drawn out from the catheter and movably containing the cannula, said protection device being configured to house said distal extremity of the cannula after the cannula has been completely detached from the catheter,
   said protection device comprising a principal body containing a movable body rotating about an axis (M) at right angles to said longitudinal axis (W) of the cannula and configured to immobilize said distal extremity of the cannula within said protection device after being completely drawn out from the catheter,
   said rotating moving body having an interacting part configured to interact with a fixed part of the catheter holder during such extraction, said interaction bringing about rotation of the rotating movable body within said principal body and immobilizing the distal extremity of the cannula within the principal body,
   wherein the principal body of the protection device comprises a cavity configured to contain said rotating movable body, said principal body comprising a channel close to such cavity,
   said channel being configured to contain the interacting part of said rotating movable body which interferes with the fixed part of the catheter holder, said channel being bounded by arms which are resiliently movable with respect to each other and configured to immobilize the interacting part of said rotating movable body after said rotating movable body has rotated within the cavity of the principal body.

2. The safety catheter needle according to claim 1, wherein the arms have projections facing each other within the channel at free extremities of the arms.

3. The safety catheter needle according to claim 1, wherein said arms have deformations configured to restrict said channel to immobilize the interacting part of said rotating movable body which interacts with the fixed part of the catheter holder after said rotating movable body has rotated within the principal body.

4. The safety catheter needle according to claim 1, wherein at least said principal body of said protection device is made from a self-lubricating low-friction plastic material.

5. The safety catheter needle according to claim 1, wherein said principal body and said rotating movable body have respectively a longitudinal cavity and a hole configured to movably contain said cannula, the longitudinal cavity of the principal body having a proximal opening of dimensions smaller than those of the deformed part of the cannula thereby preventing the distal extremity of the cannula from emerging from the longitudinal cavity after the cannula has been drawn out from the catheter, said principal body having a support for said deformed part of the cannula on said proximal opening bringing about movement of said principal body within the catheter holder while the cannula is drawn out from the catheter.

6. The safety catheter needle according to claim 1, wherein the interacting part of the rotating moving body which interacts with the fixed part of the catheter holder is an eccentric lateral projection of said rotating movable body.

7. The safety catheter needle according to claim 6, wherein said eccentric lateral projection has an upside-down L shape.

8. The safety catheter needle according to claim 1, wherein said fixed part of the catheter holder is a step within the catheter holder associated with an enlarged part within the catheter holder, said catheter holder being of a single piece.

9. The safety catheter needle according to claim 1, wherein said fixed part is defined by joining together two components defining the catheter holder, said fixed part being defined by one extremity of one of such two components.

10. The safety catheter needle according to claim 1, wherein said rotating movable body is of cylindrical shape or of a shape approximating to a solid of revolution, said rotating movable body having a longitudinal axis (Z) at right angles to said rotation axis (M), said longitudinal axis (Z) substantially coinciding with said longitudinal axis (W) of the cannula, said rotation axis (M) of said rotating movable body coinciding with the axis of rotation of such rotating movable body in the principal body.

11. The safety catheter needle according to claim 1, wherein at least said principal body of said protection device is made from metal, and said principal body having deformations bounding the cavity to contain said rotating movable body.

\* \* \* \* \*